(12) United States Patent
Ijuin et al.

(10) Patent No.: US 8,796,628 B2
(45) Date of Patent: Aug. 5, 2014

(54) METHOD AND APPARATUS FOR INSPECTING SEALING DEFECT OF CONTAINER

(75) Inventors: Taichi Ijuin, Sagamihara (JP); Tomio Yamauchi, Sagamihara (JP); Akira Kawazoe, Sagamihara (JP); Tetsuya Takatomi, Sagamihara (JP)

(73) Assignee: Daiwa Can Company, Tokyo (JP)

( * ) Notice: Subject to any disclaimer, the term of this patent is extended or adjusted under 35 U.S.C. 154(b) by 131 days.

(21) Appl. No.: 13/511,530

(22) PCT Filed: Nov. 30, 2010

(86) PCT No.: PCT/JP2010/071307
§ 371 (c)(1),
(2), (4) Date: May 23, 2012

(87) PCT Pub. No.: WO2011/068090
PCT Pub. Date: Jun. 9, 2011

(65) Prior Publication Data
US 2012/0267534 A1 Oct. 25, 2012

(30) Foreign Application Priority Data
Dec. 4, 2009 (JP) ................................. 2009-276347

(51) Int. Cl.
*G01N 21/35* (2014.01)
*G01N 21/3563* (2014.01)
*G01M 3/38* (2006.01)
*G01N 21/90* (2006.01)

(52) U.S. Cl.
CPC ............ *G01N 21/35* (2013.01); *G01N 21/9054* (2013.01)
USPC ...................................................... 250/341.8

(58) Field of Classification Search
USPC ............... 250/338.1, 340, 341.1, 341.5–8
See application file for complete search history.

(56) References Cited

U.S. PATENT DOCUMENTS

2009/0139911 A1* 6/2009 Lisec et al. .................... 209/576

FOREIGN PATENT DOCUMENTS

| JP | 62 276444 | 12/1987 |
|----|-----------|---------|
| JP | 6 144416  | 5/1994  |

(Continued)

OTHER PUBLICATIONS

JP 2000-249663 machine translation.*

(Continued)

*Primary Examiner* — David Porta
*Assistant Examiner* — Adam J Fifth
(74) *Attorney, Agent, or Firm* — Oblon, Spivak, McClelland, Maier & Neustadt, L.L.P.

(57) ABSTRACT

A method for inspecting sealing defects of a container using infrared light. Infrared light in a wavelength range of 1450 nm±20 nm is irradiated from a phototransmitter onto the sealed portion of a sample container Infrared light reflected from or transmitted through the sealed portion of the sample container is received by a photoreceiver, and transmitted to a photodetector through an optical fiber. The infrared light in a same wavelength range as the case of inspecting the sample container is irradiated onto the sealed portion of a container to be inspected. The infrared light reflected from or transmitted through the sealed portion of the inspected container is converted into the analog voltage value and transmitted to a controller. If the infrared light is reduced to be smaller than a threshold set on the basis of the sample container, the sealed portion of the inspected container is judged as a sealing defect.

10 Claims, 3 Drawing Sheets

(56) References Cited

FOREIGN PATENT DOCUMENTS

| JP | 9 96581 | 4/1997 |
|---|---|---|
| JP | 11 160185 | 6/1999 |
| JP | 2000 79917 | 3/2000 |
| JP | 2000 249663 | 9/2000 |
| JP | 2002 214361 | 7/2002 |
| JP | 2007 71568 | 3/2007 |

OTHER PUBLICATIONS

International Search Report Issued Feb. 15, 2011 in PCT/JP10/71307 Filed Nov. 30, 2010.

* cited by examiner

METHOD AND APPARATUS FOR INSPECTING SEALING DEFECT OF CONTAINER

TECHNICAL FIELD

This invention relates to a method and apparatus for inspecting sealing defects of a container which is sealed by a heat sealing method or the like, and especially to an inspecting method and an inspecting apparatus using infrared light.

BACKGROUND ART

An opening of a sac-like container called a "pouch", and an opening of a cup-shaped container closed by a sheet-like lid are sealed planewise by a heat sealing method. The opening of those containers is sealed after filling the content therein, therefore, intrusion of the contents into the sealed portion may cause a sealing defect. In order to avoid such disadvantage, the sealing defects of this kind have been detected by various methods. For example, Japanese Patent Laid-Open No. 06-144416 discloses a non-destructive and total inspecting method of heat-sealed condition using infrared radiation. According to the teachings of Japanese Patent Laid-Open No. 06-144416, the temperature at each point along the seal-width direction of the heat-sealed part is detected by an infrared ray radiation superficial thermometer without contacting with the container. In case the detected temperature distribution is different from a previously determined appropriate temperature distribution of a non-defective product more than a predetermined value, the sealed portion is judged as an unacceptable sealing.

Meanwhile, Japanese Patent Laid-Open No. 2000-79917 discloses a method of inspecting improper seal. According to the teachings of Japanese Patent Laid-Open No. 2000-79917, a temperature distribution at the seal portion just after the heat seal operation is measured by processing thermal image information taken by an infrared-ray camera. The thermal information thus measured is compared with the thermal information about the seal portion sealed properly to judge propriety of the seal portion.

DISCLOSURE OF THE INVENTION

Specifically, the heat sealing is a method of sealing a container by thermally softening adhesive agent. Therefore, as described in the above-mentioned prior art documents, sealing defects can be detected by measuring a temperature of the sealed portion or a temperature distribution in the sealed portion just after the sealing operation using infrared radiation. In this case, however, the temperature or the temperature distribution is measured utilizing the infrared radiation radiated from the hot portion. That is, in case a temperature difference between the hot portion and a periphery thereof is not sufficiently large, the temperature distribution may not be measured accurately. For example, in case it takes long time to commence an inspection of the sealed portion after the execution of the heat sealing and the sealed portion is cooled before carrying out the inspection, the temperature difference between the hot portion and the periphery thereof is eliminated. In this case, therefore, the temperature distribution in the sealed portion cannot be measured, and the propriety of the sealed portion cannot be judged.

An object of the present invention is to provide a method for inspecting sealing defects of a container, which can be carried out to inspect all of containers in a non-contact and non-destructive manner using a comparatively inexpensive apparatus, even if it is not just after a heat sealing operation.

In order to achieve the above-mentioned object, according to the present invention, there is provided a method and an apparatus for inspecting sealing defects in a sealed portion of a container sealed planewise using infrared light. Specifically, according to the present invention, the infrared light in a wavelength range of 1450 nm±20 nm is irradiated onto the sealed portion of a sample container which does not have a sealing defect. The infrared light reflected from or transmitted through the sealed portion of the sample container is received by a photoreceiver. After thus receiving the infrared light, a voltage is outputted according to an amount of the received infrared light, and the voltage thus outputted is converted into an analog voltage value thereby setting a threshold based on the analog voltage value. Likewise, the infrared light in a same wavelength range as the case of inspecting the sample container is also irradiated onto the sealed portion of a container to be inspected. The infrared light reflected from or transmitted through the sealed portion of the inspected container is also received by the photoreceiver. The infrared light thus received by the photoreceiver is also converted into the analog voltage value as in the case of the sample container, and if the analogue voltage value of the inspected container is smaller than the threshold, the sealed portion of the inspected container is judged as a sealing defect.

According the present invention, the infrared light is preferably generated using a semiconductor laser diode. In addition, a plurality of collecting lenses may be used to receive the infrared light reflected from divided areas of the sealed portion or transmitted through the divided areas of the sealed portion.

As described, according to the present invention, the infrared light in the wavelength range of 1450 nm±20 nm is irradiated onto the sealed portion of the container. In case the sealed portion is contaminated by the content containing moisture, the infrared light is absorbed by the moisture of the contaminant, and in this case, the amount of the infrared light reflected from or transmitted through the contaminated portion is reduced. Therefore, according to the present invention, the sealing defects in the sealed portion can be judged without measuring temperature distribution in the sealed portion after sealing the sealed portion by the heat sealing.

As also described, according to the present invention, not the measured amount of the infrared light reflected from or transmitted through the sealed portion, but the analog voltage value converted from the infrared light reflected from or transmitted through the sealed portion being inspected is compared with the threshold. Therefore, in addition to the above-explained advantage, such comparison of the infrared light reflected from or transmitted through the sealed portion with the threshold can be carried out using a comparatively inexpensive device for converting the infrared light into the analog voltage value, without using a comparatively expensive device for measuring the amount of the infrared light.

BEST MODE FOR CARRYING OUT THE INVENTION

Figure 1:
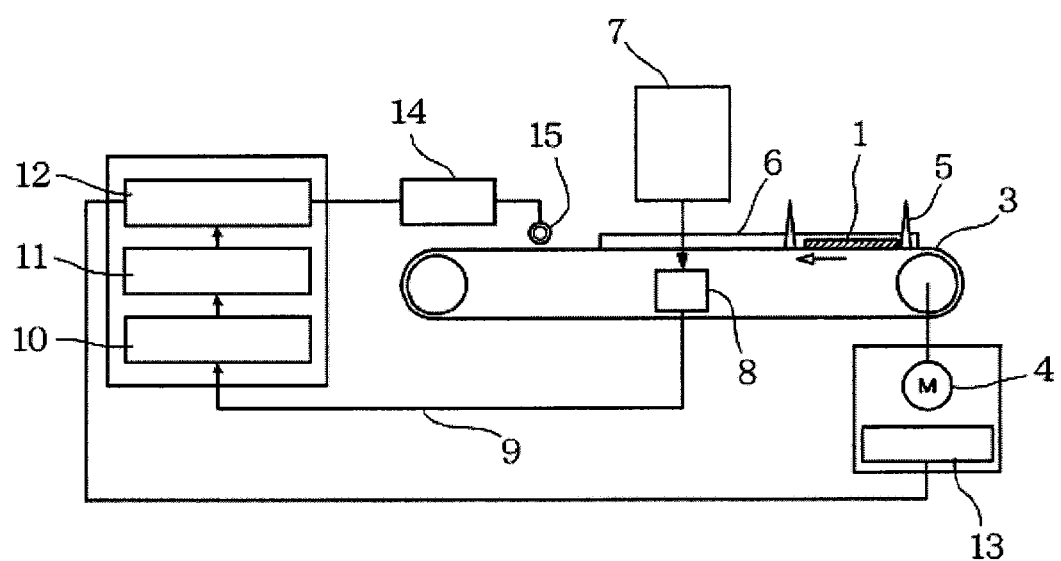
FIG. 1 is an explanatory drawing schematically showing one example of the apparatus according to the present invention configured to inspect separated containers conveyed by a belt conveyer.

The present invention is configured to detect sealing defects of containers using infrared light, and wavelength range of the infrared light is restricted within a range of 1450 nm±20 nm. In case of thus using the infrared light, all of objects can be inspected in a non-contact and non-destructive manner. Although 77% of the infrared light within the above-mentioned wavelength range is absorbed by water, such infrared radiation is not absorbed by a synthetic resin such as polyethylene (PE), polypropylene (PP), polyethylene terephthalate (PET) and so on. Therefore, a contaminant containing water in the sealed portion can be identified clearly.

Both of the infrared lights reflected from the sealed portion and transmitted through the sealed portion contain information about the sealed portion. Therefore, according to the present invention, a judgment of the sealing defect is made not only on the basis of the infrared light reflected from the sealed portion but also on the basis of the infrared light transmitted through the sealed portion.

In addition, the infrared light can be converted easily into the analog voltage using an inexpensive device. Therefore, the present invention is configured to convert the infrared light reflected from or transmitted through the sealed portion into analog voltage, and to judge the propriety of the sealed portion based on the analog voltage thus converted.

Specifically, according to the present invention, the propriety of the sealed portion is judged not on the basis of an absolute value of the analog voltage, but on the basis of a relative value of the analog voltage. This is because a reflecting amount and a transmitting amount of the infrared light are varied depending on a structure and material of the sealed portion. Therefore, the present invention is configured to irradiate the infrared light in the above-mentioned wavelength range onto the sealed portion of a sample container which does not have a sealing defect, and to convert the infrared light reflected from or the transmitted through the sealed portion into the analog voltage thereby setting a threshold based on the analogue voltage thus converted. The threshold thus obtained is used to judge the propriety of the sealed portion.

Thus, the method and the apparatus according to the present invention is configured to inspect the sealed portion closed by bonding an opening of the container. However, since the infrared radiation is thus used to inspect the sealed portion, the sealed portion has to be made of the material transmissive to the infrared light to an adhesive site, or has to be structured to allow the infrared light to penetrate therethrough to the adhesive site. Here, both sac-like container and cup-shaped container can be inspected by the present invention.

Hereinafter, an example of inspecting cylindrical sac-like containers is to be explained. Specifically, the sac-like container to be inspected contains content in a cylindrical portion thereof, and both ends of the cylindrical portion are sealed by a heat sealing method. Preferably, all of the containers thus structured are inspected continuously not only during a manufacturing process but also after filling the content therein.

Here will be briefly explained a manufacturing process of the sac-like container. First of all, an endless synthetic resin sheet material is rolled in a manner to wrap around a nozzle of a filling device for filling the content, and overlapped end portions of the rolled sheet are sealed longitudinally by the heat sealing. Then, one of the end portions of the cylindrical body thus formed is sealed widthwise by the heat sealing, and the content is filled in the cylindrical body from the other end portion. The other end portion is then sealed by the heat sealing to complete the sac-like container. The above-explained procedure is carried out repeatedly while feeding the synthetic resin sheet material continuously. As a result, a plurality of sac-like containers connected through the sealed portions are produced, and then, the connected containers are separated by cutting an appropriate portion of the sealed portion.

In order to prevent intrusion of contaminants into the sealed portion of the sac-like container, the contents and the air interposing in the portion to be sealed by the heat sealing have to be pushed out. For this purpose, after filling the content into the container, the heat sealing is applied to the portion to be sealed gradually from inside of the container toward outside of the container using a sealing mold. Alternatively, the portion to be sealed by the heat sealing is squeezed by a roller in advance, and then sealed by the sealing mold.

However, in case liquid content containing solid contents is contained in the container, for example, in case tuna and mayonnaise prepared by mixing flaked tuna with mayonnaise is contained in the container, the solid content interposing in the portion to be sealed by the heat sealing is difficult to be pushed out. In this case, therefore, the sealed portion may be contaminated by the solid contents remaining therein. As a result, mold may be grown in the sealed portion, and in addition, leakage of the content may occur. Therefore, it is desirable to inspect the sealed portions of all of the produced containers.

Thus, according to the present invention, the sealed portion of the containers in which both ends of the cylindrical portion containing the content are sealed by the heat sealing is inspected. Specifically, the method and apparatus according to the present invention are configured to inspect the sealed portions of all of the produced containers using infrared light in a continuous manner. An example thereof will be explained hereinafter in more detail.

Figure 2:
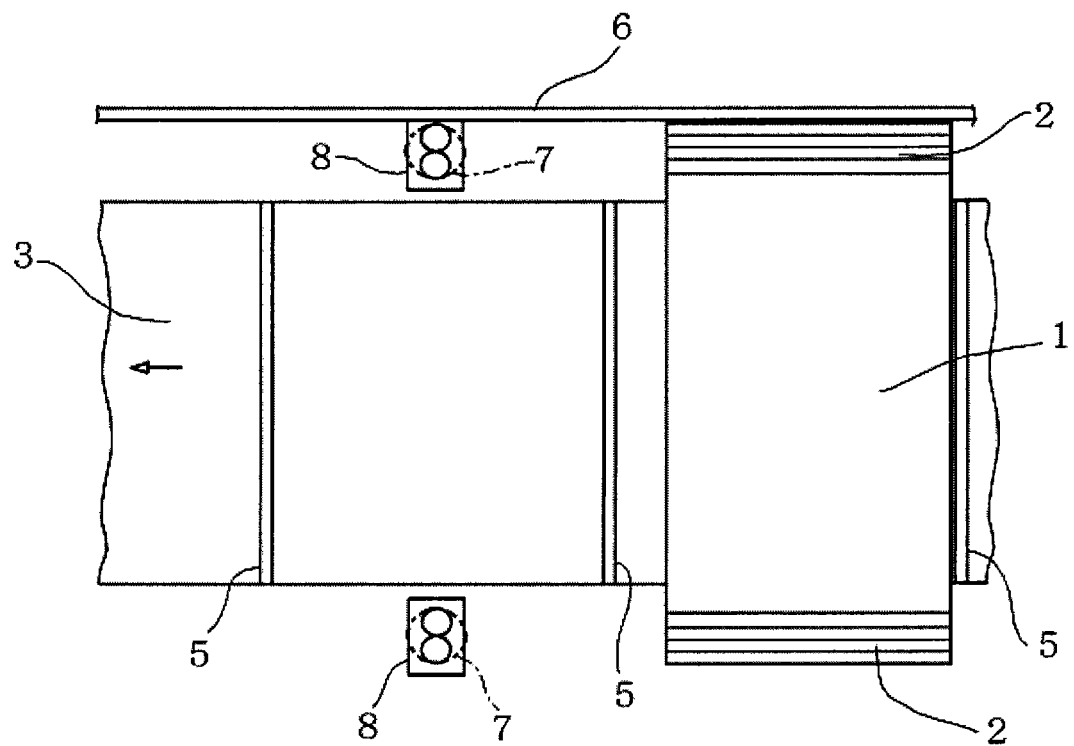
FIG. 2 is an explanatory drawing showing a phototransmitter for irradiating the infrared light and a photoreceiver for receiving the infrared light used in the apparatus shown in FIG. 1.

First of all, the inspecting apparatus according to the present invention will be explained hereinafter. FIGS. 1 and 2 are explanatory drawings schematically showing the inspecting apparatus according to the present invention, which is configured to inspect a sealed portion 2 of a sac-like container 1 while conveying the sac-like containers 1 continuously. Specifically, the sac-like container 1 is a single layered container made of polypropylene, and separated into a single container having the sealed portion 2 on both ends. A size of the container 1 should not be limited to a specific size. In this example, specifically, a width of the container 1 is 50 mm, a length of the container 1 is 100 mm, and a width of the sealed portion 2 in the longitudinal direction is 10 mm. However, for example, a single layered container made of polyethylene terephthalate, a multi-layered container in which a gas-barrier resin layer such as copolymer nylon or ethylene vinyl alcohol layer is interposed between polyethylene terephthalate or polypropylene layers and so on may also be inspected by the present invention. Thus, according to the present invention, size and material of the container are not especially limited.

In order to convey the containers 1 continuously, the inspecting apparatus is provided with a belt conveyer 3. Specifically, the belt conveyer 3 is configured to be driven by a motor 4 at a constant speed, and the container 1 is laid on the conveyer 3 transversely with respect to a traveling direction of the belt conveyer 3, that is, the container 1 is laid on the conveyer 3 in a manner to situate the sealed portions 2 on both lateral sides of the belt conveyer 3. On an upper face of the belt conveyer 3, a plurality of push fins 5 are formed at regular intervals in the traveling direction, and a guide 6 is arranged in parallel with the belt conveyer 3. Therefore, the container 1 laid on the belt conveyer 3 is conveyed by the belt conveyer 3 at a constant speed while being pushed by the push fin 5, and a lateral posture of the container 1 being conveyed is maintained by the guide 6.

A pair of phototransmitter 7 and photoreceiver 8 is arranged on each side of the belt conveyer 3 in a running route of the belt conveyer 3. Specifically, those phototransmitter 7 and photoreceiver 8 are arranged to be opposed to each sealed portion 2 of the container 1 being conveyed while being guided by the guide 6. The phototransmitter 7 is configured to irradiate the infrared light in a wavelength range of 1450 nm±20 nm to the sealed portion 2. Specifically, the phototransmitter 7 irradiates the infrared light in a circular form of approximately 10 mm diameter onto the sealed portion 2 entirely widthwise (i.e., in a direction perpendicular to the conveying direction).

For example, in order to irradiate the infrared light from the phototransmitter 7, an infrared-emitting diode may be used. In this case, however, the wavelength of the irradiated infrared light may be broadened from the initial wavelength. Therefore, it is preferable to use a laser diode in the phototransmitter 7 to irradiate the infrared light. In this case, an inspecting accuracy may be improved to restrict the wavelength of the infrared light irradiated from the laser diode within a range of 1450 nm±20 nm.

Meanwhile, the photoreceiver 8 is configured to receive the infrared light transmitted through the sealed portion 2. Specifically, according to this example, the photoreceiver 8 is provided with two collecting lenses arranged in the width direction of the sealed portion 2. As described, the phototransmitter 7 is configured to irradiate the infrared light in a circular form of approximately 10 mm diameter. However, the diameter of the infrared light after penetrating through the sealed portion 2 is enlarged slightly. Therefore, the collecting lenses individually having a diameter of 6 mm are used in the photoreceiver 8.

Alternatively, it is also possible to use only one collecting lens (having a diameter of 12 mm) in the photoreceiver 8. However, in case of using two collecting lenses (having a diameter of 6 mm each), an inspecting area of each collecting lens may be reduced. In this case, therefore, the inspecting accuracy can be improved in comparison with the case in which only one collecting lens is used. In addition, in case of detecting finer contaminants, such finer contaminants can be detected using larger number of collecting lenses having smaller diameters.

The photoreceiver 8 is connected with a photodetector 10 through an optical fiber 9. Therefore, the infrared light received by photoreceiver 8 is transmitted to the photodetector 10 through an optical fiber 9. As described, according to the example, two collecting lenses are arranged on both sides of the belt conveyer 3 (i.e., total four collecting lenses are arranged). Therefore, four photodetectors 10 are used in this example. Specifically, the photodetector 10 is configured to output a voltage as a detection signal in accordance with an amount of the received infrared light. The voltage signal outputted from the photodetector 10 is converted into an analog voltage value by a smoothing circuit board 11, and the analog voltage value thus converted is transmitted to a controller 12. Accordingly, the photodetector 10 and the smoothing circuit board 11 correspond to a voltage generating means of the present invention. For example, the controller 12 is composed mainly of a microcomputer, and an output signal from an encoder 13 attached to a motor 4 is inputted thereto. Specifically, the controller 12 is configured to judge the propriety of the sealed portion 2 by processing the signal inputted thereto, and to output a control signal based on the judgment result. In this example, a reject nozzle 15 is arranged in a downstream side of the conveying direction of the belt conveyer 3. The reject nozzle 15 is configured to spray compressed air to the container 1 being conveyed on the belt conveyer 3 when an air passage is opened by a solenoid valve 14, and for this purpose, the control signal of the controller 12 is inputted to the solenoid valve 14. Accordingly, the controller 12 corresponds to the threshold holding means, the comparing means, and the judging means of the present invention.

Next, here will be explained an inspecting method of the present invention using the above-explained apparatus. First of all, the infrared light is irradiated to the sealed portion 2 of the sample container 1 which is sealed properly, and data thereof is collected on the basis of the infrared light reflected from the sealed portion 2 or transmitted through the sealed portion 2. The data about the sealed portion which does not have a sealing defect thus obtained is used as reference data (i.e., a threshold). For this purpose, specifically, the container 1 which does not have a sealing defect is conveyed by the belt conveyer 3, and the infrared light in the wavelength range of 1450 nm±20 nm is irradiated to the sealed portion 2 from the phototransmitter 7.

The infrared light irradiated from the phototransmitter 7 is transmitted through the sealed portion 2 of the container 1 and received by photoreceiver 8. The infrared light thus received by the photoreceiver 8 is transmitted through the optical fiber 9 to the photodetector 10, and the photodetector 10 outputs the voltage in accordance with (i.e., in proportional to) the amount of the infrared light transmitted thereto. Then, the voltage outputted from the photodetector 10 is converted into an analog voltage value by the smoothing circuit board 11 and further transmitted to the controller 12. The analog voltage value thus transmitted to the controller 12 is stored into the controller 12 as a threshold.

The analog voltage value transmitted from the smoothing circuit board 11 to the controller 12 may be changed depending on the entire structure of the inspecting apparatus, an output of the phototransmitter 7, a specification of the photoreceiver 8 and so on. According to the example, specifically, a maximum value of the analog voltage value transmitted from the smoothing circuit board 11 to the controller 12 is 10V and a minimum value is 0V. Specifically, the analog voltage value is proportional to the amount of the infrared light transmitted through the sealed portion 2, therefore, the analog voltage value becomes the maximum value, that is becomes 10V in case the infrared light is transmitted through the sealed portion sealed properly. Therefore, the threshold of the analog voltage value used in this example is 10V.

In addition, a plurality of thresholds may be set for different points in the inspecting area of the sealed portion 2 by arranging a plurality of the light collecting lenses in the photoreceiver 8. In this case, a desired point in the sealed portion 2, e.g., a central portion of the sealed portion 2 can be inspected more precisely. Therefore, for example, the inspecting apparatus may be configured not to judge the sealed portion 2 as defective even if an outer edge of the sealed portion 2 is contaminated little bit but the central portion thereof is sealed substantially properly.

After thus setting the threshold of the analog voltage value, the containers 1 are conveyed by the belt conveyer 3 continuously to be inspected. In this situation, the infrared light in a wavelength range of 1450 nm±20 nm is irradiated to the sealed portion 2 of the container 1 being conveyed from the phototransmitter 7 in the same amount as the case of inspecting the sample container. The infrared light transmitted through the sealed portion 2 of the container 1 is received by the photoreceiver 8, and further transmitted to the photodetector 10 through the optical fiber 9. Then, the infrared light is converted into the analog voltage value by the smoothing circuit board 11 and transmitted to the controller 12.

The analog voltage value of the inspected sealed portion 2 of the container 1 thus transmitted to the controller 12 is compared with the threshold of the analog voltage value set in advance. Specifically, in case the analog voltage value of the inspected sealed portion 2 is smaller than the threshold value, the inspected sealed portion 2 is judged as a sealing defect. According to the example, in case the sealed portion 2 is thus judged as the sealing defect, a rejection signal is outputted from the controller 12.

To the controller 12, positional information is inputted from the encoder 13 attached to the motor 4 driving the belt conveyer 3. Specifically, the information about positions of the containers 1 on the belt conveyer 3 is inputted to the controller 12. Therefore, the container 1 having a defected sealed portion 2 conveyed to the reject nozzle 15 can be discriminated based on the positional information inputted to the controller 12. The controller 12 outputs the rejection signal to open the solenoid valve 14 at a timing when the container 1 having a sealing defect on its sealed portion 2 reaches in front of the reject nozzle 15. Consequently, only the container 1 having a sealing defect on its sealed portion 2 is ejected from the belt conveyer 3 by the compressed air blown from the reject nozzle 15.

The present intervention should not be limited to the examples thus far explained, and may be modified arbitrarily according to need. For example, in the above-explained examples, the inspecting apparatus is configured to inspect the sealing defects of the separated sac-like containers continuously while conveying the containers by the belt conveyer. However, as shown in FIG. 3, the inspecting apparatus may also be configured to inspect the containers 1 connected through the sealed portions 2 before separated into single containers 1.

Figure 3:
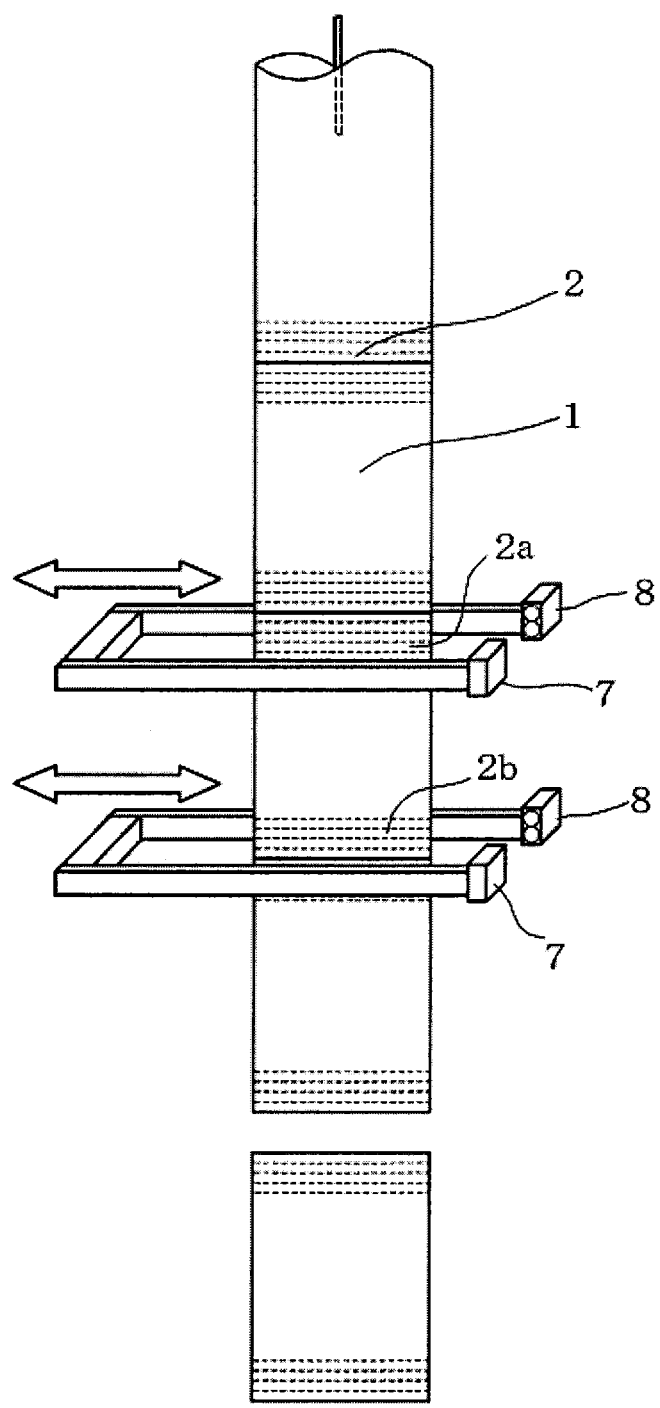
FIG. 3 is an explanatory drawing schematically showing another example of the phototransmitter for irradiating the infrared light and a photoreceiver for receiving the infrared light.

As shown in FIG. 3, in case of inspecting the sealed portions 2 of the containers 1 connected through the sealed portion 2, a pair of phototransmitter 7 and photoreceiver 8 are arranged to be opposed to each other across an upper sealed portion 2a of the container 1 at a predetermined position, and another pair of phototransmitter 7 and photoreceiver 8 are arranged to be opposed to each other across a lower sealed portion 2b of the container 1 at the predetermined position. Both pairs of the phototransmitter 7 and photoreceiver 8 are allowed to be reciprocated in a width direction of the container 1 (i.e., in the horizontal direction of FIG. 3). In this case, the phototransmitter 7 irradiates the infrared light in the above-mentioned wavelength range to the sealed portion 2, and the photoreceiver 8 receives the infrared light transmitted through the sealed portion 2, while being moved in the width direction of the container 1. Then, the propriety of the sealed portion 2 is judged based on an amount of the infrared light transmitted through the sealed portion 2 by the above-explained procedure. In this case, the inspection of the sealed portion 2 can be carried out during a manufacturing process, a filling process, a sealing process and separating process of the containers 1.

In addition, the present invention may be used not only to inspect the sac-like container but also used to inspect other kinds containers such as a cup-shaped container closed by a sheet shaped lid body. Moreover, the present invention may be used not only to inspect the sealed portion sealed by the heat sealing but also to inspect the sealed portion sealed planewise by the other kinds of methods. Although not especially shown, in case of inspecting the sealed portion of the cup-shaped container which is closed by the sheet shaped lid body after filling a content therein, the infrared light is irradiated to a flat-ring shaped sealed portion extending horizontally and outwardly from an opening end of the cup-shaped container while conveying a plurality of the cup-shaped containers continuously.

Further, the present invention should not be limited to be configured to irradiate the infrared light onto the sealed portion from the phototransmitter, and to receive the infrared light transmitted through the sealed portion by the photoreceiver. For example, although not especially shown, a light receiving and emitting device may also be used instead of the phototransmitter and the photoreceiver. In this case, the infrared light is irradiated to the sealed portion from the light receiving and emitting device, and the light receiving and emitting device also receives the infrared light reflected from the sealed portion. The inspecting apparatus thus structured is capable of inspecting the sealed portion made of a material which reflects a semiconductor laser light, such as a material prepared by laminating a thermoplastic resin film onto an aluminum foil or an iron foil, a material prepared by applying a thermoplastic resin coating on an aluminum foil or an iron foil, a material prepared by evaporating metal onto a thermoplastic resin film and so on.

The invention claimed is:

1. A method for inspecting sealing defects in a sealed portion of a container sealed planewise using infrared light, comprising:
    irradiating the infrared light in a wavelength range of 1450 nm±20 nm onto a sealed portion of a sample container from an outside of the sample container, which does not have a sealing defect and which includes a content therein, the sample container being sealed after being filled with the content;
    receiving the infrared light reflected from or transmitted through the sealed portion of the sample container at the outside of the sample container;
    outputting a voltage according to an amount of the received infrared light;
    converting the outputted voltage into an analog voltage value thereby setting a threshold based on the analog voltage value;
    irradiating the infrared light onto the sealed portion of a container to be inspected, which container is filled with the content and sealed, the infrared light being in a same wavelength range as is irradiated onto the sealed portion of the sample container and being irradiated from an outside of the container;
    receiving the infrared light reflected from or transmitted through the sealed portion of the inspected container at the outside of the container;
    converting the received infrared light into the analog voltage value as in the case of the sample container; and
    judging a sealing defect in case the analogue voltage value is smaller than the threshold.

2. The method for inspecting sealing defects in a sealed portion of a container as claimed in claim 1, wherein the infrared light includes an infrared light of a semiconductor laser diode.

3. The method for inspecting sealing defects in a sealed portion of a container as claimed in claim 2, wherein a plurality of collecting lenses are used to receive the infrared light reflected from divided areas of the sealed portion or transmitted through the divided areas of the sealed portion.

4. The method for inspecting sealing defects in a sealed portion of a container as claimed in claim 1, wherein a plurality of collecting lenses are used to receive the infrared light reflected from divided areas of the sealed portion or transmitted through the divided areas of the sealed portion.

5. The method for inspecting sealing defects in a sealed portion of a container as claimed in claim 1, wherein the irradiating of the infrared light is performed on a first side of the sealed portion of the container, and the receiving the infrared light is performed on a second side of the sealed portion of the container, the second side being opposite the first side.

6. An apparatus for inspecting sealing defects in a sealed portion of a container sealed planewise using infrared light, comprising:
- a phototransmitter, which irradiates the infrared light in a wavelength range of 1450 nm±20 nm onto the sealed portion of the container, the container including a content therein, and the container being sealed after being filled with the content;
- a photoreceiver, which receives the infrared light reflected from or transmitted through the sealed portion of the container at an outside of the container;
- a voltage generating means, which outputs an analog voltage value according to an amount of the received infrared light;
- a threshold holding means, which sets a threshold based on an analog voltage value outputted from the voltage generating means in a case where the infrared light is irradiated onto a sealed portion of a sample container and being irradiated from an outside of the sample container, which sample container does not have a sealing defect;
- a comparing means, which compares an analog voltage value outputted from the voltage generating means in a case where the infrared light is irradiated onto the sealed portion of the container being inspected with the threshold; and
- a judging means, which judges that a sealing defect exists when the analog voltage value outputted from the voltage generating means in the case where the infrared light is irradiated onto the sealed portion of the container being inspected is smaller than the threshold.

7. The apparatus for inspecting sealing defects in a sealed portion of a container as claimed in claim 6, wherein the infrared light includes an infrared light of a semiconductor laser diode.

8. The apparatus for inspecting sealing defects in a sealed portion of a container as claimed in claim 7, further comprising:
- a plurality of collecting lenses used to receive the infrared light reflected from divided areas of the sealed portion or transmitted through the divided areas of the sealed portion.

9. The apparatus for inspecting sealing defects in a sealed portion of a container as claimed in claim 6, further comprising:
- a plurality of collecting lenses used to receive the infrared light reflected from divided areas of the sealed portion or transmitted through the divided areas of the sealed portion.

10. The apparatus for inspecting sealing defects in a sealed portion of a container as claimed in claim 6, wherein the phototransmitter is disposed on a first side of the sealed portion of the container, and the photoreceiver is disposed on a second side of the sealed portion of the container, the second side being opposite the first side.

* * * * *